United States Patent [19]
Roberts

[11] Patent Number: 5,951,591
[45] Date of Patent: Sep. 14, 1999

[54] BACK-MOUNTED MOBILE BACK SUPPORT DEVICE

[76] Inventor: Bruce Roberts, P.O. Box 1087, Aptos, Calif. 95001

[21] Appl. No.: 09/018,412

[22] Filed: Feb. 4, 1998

[51] Int. Cl.[6] ............................................. A61F 5/00
[52] U.S. Cl. ............................................. 606/241; 602/36
[58] Field of Search ................... 602/19, 32, 36; 128/99.1, 102.1, 103.1, 105.1; 606/241; 2/44, 45, 92

[56] References Cited

U.S. PATENT DOCUMENTS

| | | | |
|---|---|---|---|
| 654,173 | 7/1900 | Mendenhall | 2/45 X |
| 1,202,851 | 10/1916 | Kelly | 2/45 X |
| 1,371,690 | 3/1921 | Kelly | 2/45 X |
| 1,409,326 | 3/1922 | Williamson | 2/45 X |
| 1,678,584 | 7/1928 | Branson | 2/45 X |
| 3,003,498 | 10/1961 | Hotas | 602/36 |
| 4,458,784 | 7/1984 | Holmes, Jr. . | |
| 4,829,989 | 5/1989 | Deamer et al. . | |
| 4,905,678 | 3/1990 | Cumins et al. . | |
| 5,022,622 | 6/1991 | Schaevitz . | |
| 5,060,754 | 10/1991 | Feick . | |
| 5,176,622 | 1/1993 | Anderson et al. . | |
| 5,199,940 | 4/1993 | Morris et al. | 602/19 |
| 5,259,833 | 11/1993 | Barnett . | |
| 5,322,409 | 6/1994 | McCluney . | |

*Primary Examiner*—Linda C. M. Dvorak
*Attorney, Agent, or Firm*—Carol D. Titus; James J. Leary

[57] ABSTRACT

A mobile back mounted supporting device for relieving pressure off of the back of a person who has to endure frequent bending. This device permits a wearer to bend over and remain parallel to the ground for extended periods of time without discomfort. It allows maximum movement for the operator since the operating parts do not get in the way. This device consists of a frame to which a chest harness, belt clip, and leg extensions are attached. The chest harness is worn by the worker and is supported by a system of elastic cord and pulleys. The harness pulls up on the upper body as the worker bends forward and thus provides support. The farther the wearer bends forward, the more tension is placed on the cords, and thus more support is given to the back.

19 Claims, 4 Drawing Sheets

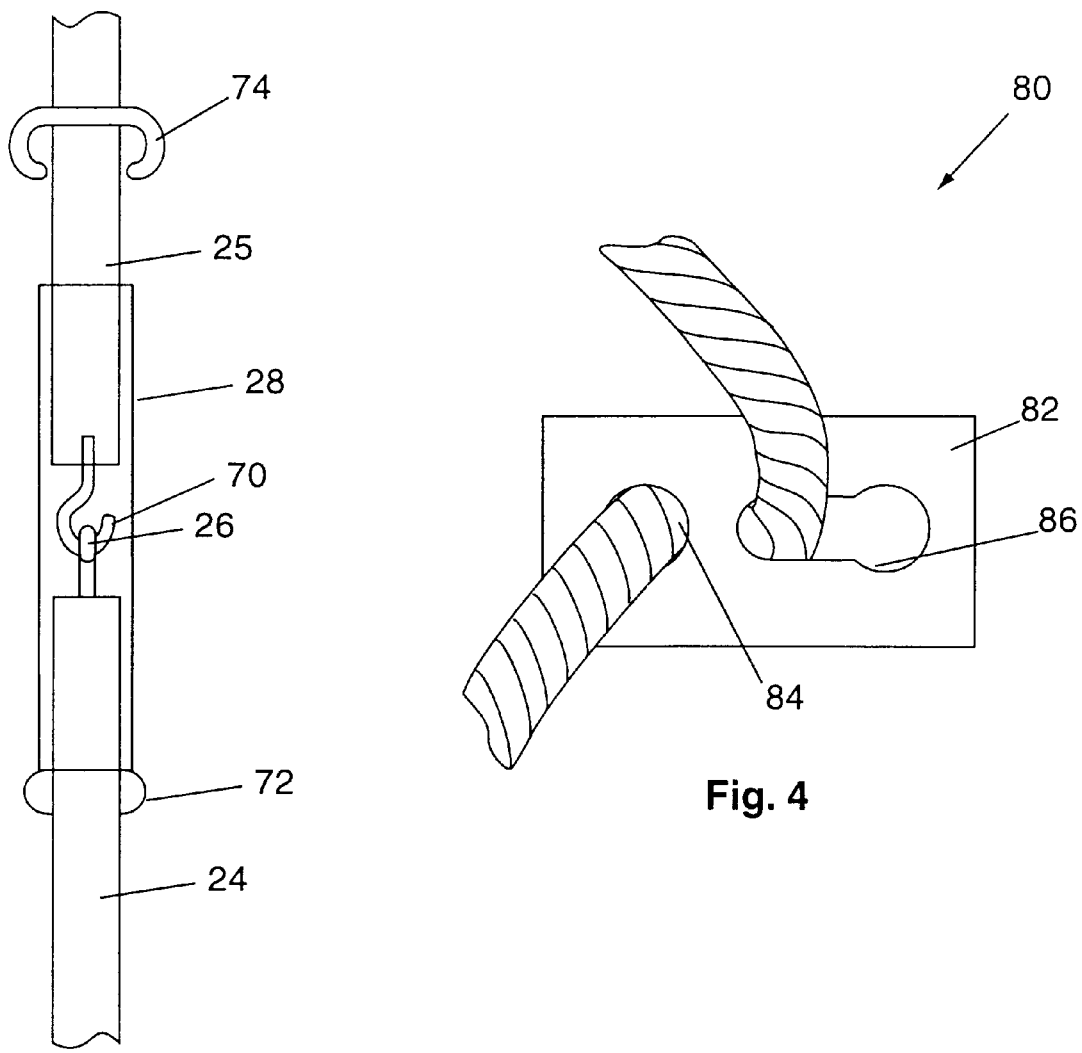

BACK-MOUNTED MOBILE BACK SUPPORT DEVICE

FIELD OF INVENTION

The present invention relates to a wearable apparatus for supporting the lower back of people who must operate in a stooped position or who must repetitively stoop or bend at the waist.

BACKGROUND OF THE INVENTION

The lower back is one of the weakest points of the human body. There are many situations in which a worker is required to repeatedly bend over or stoop to pick up an object from ground level. This situation is commonly seen in the agriculture industry where workers frequently have to bend over repetitively for several hours at a time. This type of work may result in the development of chronic back pain or repetitive strain injury.

Prior art devices have attempted to address this problem. For example, in U.S. Pat. No. 4,458,784, Holmes describes a device which supports a person's upper torso weight when kneeling or stooping. However, this device must be inserted into the ground near where a person works, and therefore, must be moved and reinserted into the ground every time the worker changes location. This is a disadvantage for a user who needs to move frequently.

U.S. Pat. No. 5,322,409 discloses a harvest machine which a user moves along the ground using wheels. A worker is supported by harnesses that hang from the top of a vertical frame. The vertical frame is attached to another frame parallel to the ground which has wheels attached. The wheels allow for the person to move the machine only in a straight line while working. The machine is bulky and must move to wherever the user wishes to work. Therefore, it would be inconvenient or impossible to use in difficult terrain or if the user needed relatively fine control over his or her motion, or if the user needs to move frequently or in a more random pattern. Work is further impaired if the worker must travel a long distance between different work sites since the worker must pull the cart.

U.S. Pat. Nos. 5,259,833; 4,829,989; and 5,176,622 are all examples of devices that are attached only to the worker's body. U.S. Pat. No. 5,259,833 illustrates an apparatus that prevents the body from bending inappropriately while in use. However, it restricts all rotation and only allows the user to bend forward and does not provide any additional support to the back. U.S. Pat. Nos. 4,829,989 and No. 5,176,622 are examples of devices attached only to the hip of the worker and function by pressing simultaneously up against the chest and down against upper legs of the worker when the worker is bent forward. However, when the person is completely upright, the support pieces remain in front of the legs and chest and would interfere with normal walking.

SUMMARY OF THE INVENTION

The present invention not only provides back support but does so in a manner that does not hinder the upper or lower body movements of the user. The undesirable force placed on the lower back when a worker is stooped over is redirected to the legs and buttocks. Also, the device is designed to provide the operator with increased comfort, which may increase productivity and reduce fatigue and injury.

The device consists of a rigid or flexible frame which can be made of metal, fiberglass, or equivalent structural material depending on the application. The length of the frame, which is adjustable, extends from the back of the knees to about shoulder height. Attached to the frame by means of a pulley and cable spring system is a harness which engages the user's chest. The harness is shaped like a vest and is easily donned and removed by using hook and loop fastener straps, shoelace-like ties, compression straps, buckles, or other such means which are located down the middle of the front side of the vest. This will allow for a secure and comfortable fit. The material for the harness should be strong, lightweight, and flexible to avoid restricting movement of the operator's arms. Since the harness covers such a large portion of the upper body, it is preferably formed of a washable and breathable material for maximum comfort. The harness may attach to extension springs that are directed by two pair of pulleys. The extension springs provide tension but still allow relative movement between the harness and the user. The springs are mounted securely to the back side of the frame and are out of the way so as not to obstruct movement. The springs can be replaced with bungee cords, or other similar materials, depending on the application, and are adjusted by a clip that controls the amount of tension present. One set of pulleys are mounted into the top portion of the frame. A second set of pulleys are located on extensions which extend back from the frame.

The frame is coupled to the operator at the waist by a pair of belt clips. It is made of a comfortable and durable material and is able to support the weight of the frame. The belt clips are clips to the belt or waistband of a user's pants to hold the back support device during the donning process. The frame is also attached to the wearer at the legs with leg straps. The vertical members of the frame are not a single piece, rather they are separated into two sections connected at a pivot point. A hollow sleeve encircles the pivot point and a portion of each of the two sections thereby creating the rigid support. When the sleeve is slid away from the pivot point, the two rod pieces are able to bend at the pivot and the operator has unrestricted movement of the legs to allow for easy walking. Without the sleeve, the operator would be restricted to the frame and would not be able to move freely. The leg straps are attached to the vertical members and are preferable made out of a durable, washable material such as canvas or nylon. The leg straps may attach above or below the knee and can use any one of a number of available fastening devices including hook and loop fastening material.

When a user is wearing the present invention, the back is being supported comfortably and without obstruction. As the wearer bends forward, the cables and springs, which provide the tension, pull up on the harness thus creating the support needed, by transferring the user's upper body weight to the legs and buttocks.

This device differs from other devices because it is completely mobile and can move with the user to any location and it is mounted on the back of an operator instead of the front. Therefore, it is out of the way of arm, leg, and waist movement.

BRIEF DESCRIPTION OF THE DRAWINGS

FIG. 3 is a cutaway enlarged view of the pivot point of vertical frame members with the hollow sleeve.

FIG. 4 is a cutaway enlarged view of a clip which controls the tension of the elastic cord.

DETAILED DESCRIPTION OF THE INVENTION

Figure 1:
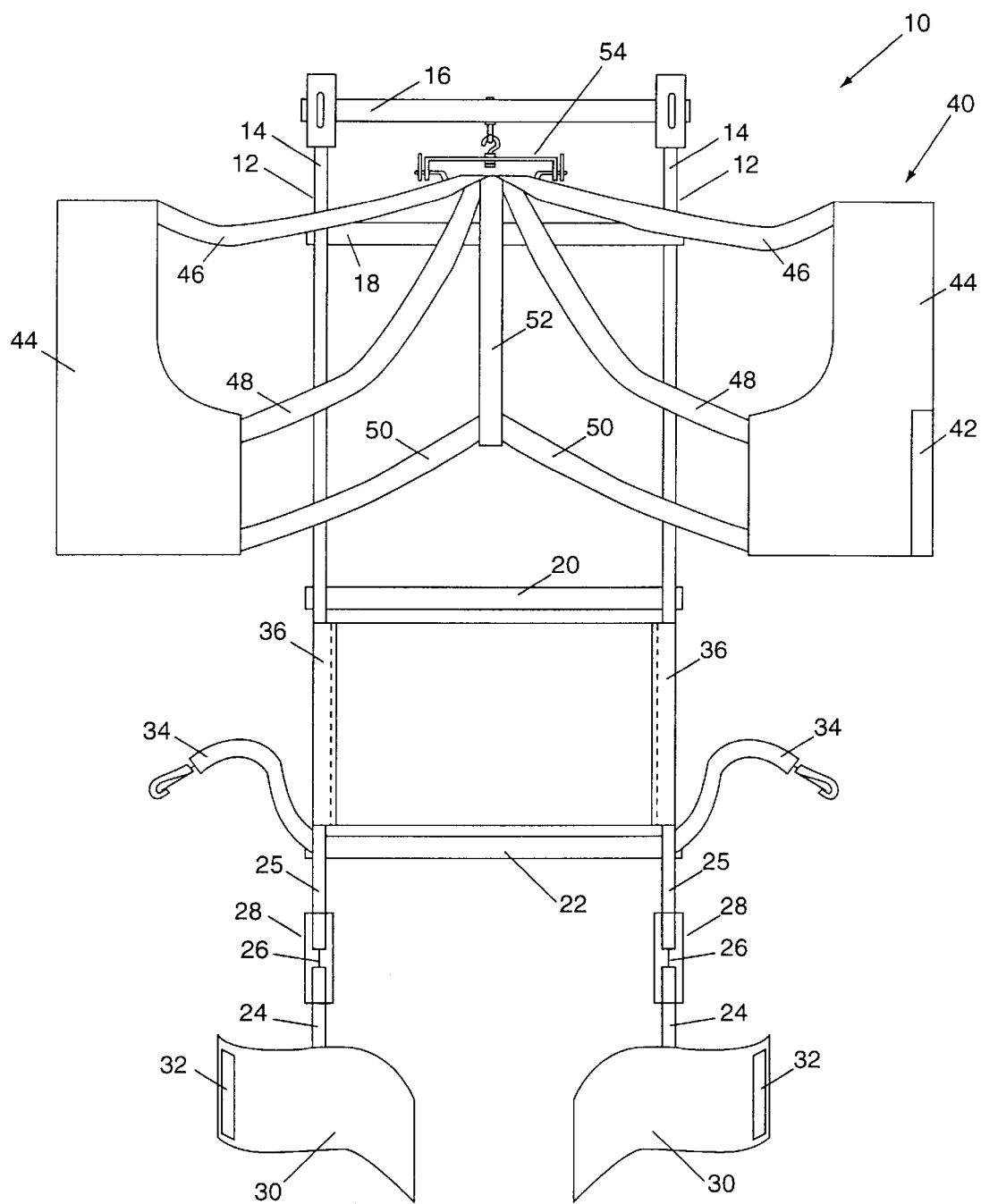
FIG. 1 is a front view of the present invention with all body attachments opened.
Figure 2:
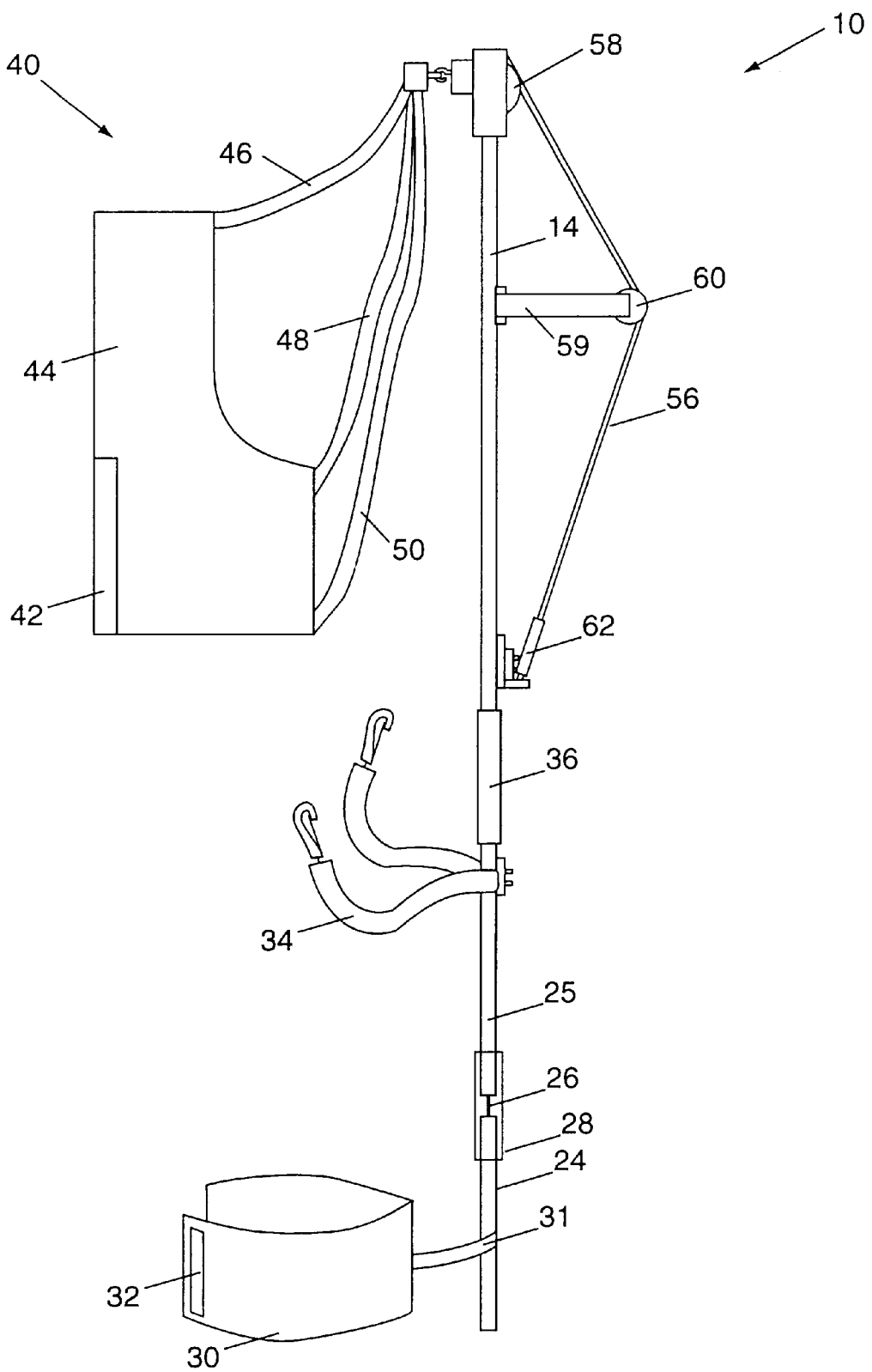
FIG. 2 is a side view of the present invention.

FIGS. 1 and 2 show a first embodiment of the back support device 10, having the following major parts a frame 12, a harness 40, and various attachments for attaching the back support device 10 to the user. In the embodiment shown, the frame 12 has two vertical members 14 which form the left and the right sides of the device 10. Each vertical member 14 has an upper section 25 and a lower section 24. A plurality of horizontal members 18, 20, 22 connect the vertical members 14. In the current embodiment there are three horizontal members, an upper horizontal member 18, a intermediate horizontal member 20, and a lower horizontal member 22. Although other materials may be used, in the present embodiment the frame 12 members are all formed of a relatively rigid or flexible material, such as metal, plastic, wood, fiberglass etc. A lightweight flexible material such as fiberglass is preferred, although any material which is sufficiently stiff and lightweight may be used.

The harness 40 is formed of a plurality of straps and two front sections 44. The front sections 44 attach to each other along the middle edge by any convenient attachment means, including ties, buckles, hook and loop fastener, snaps, etc. in a manner similar to a vest. The configuration shown has three pair of straps which extend between the outer edges of the right and left front sections 44 and the bracket 54. The first pair 46 are shoulder straps and extend over the shoulder of the user. The second pair 48 are intermediate straps and extend under the arm about midway down the chest. The third pair 50 are waist straps and extend back from the user's waist. The waist straps 50 both attach to the base of a harness bar 52. The shoulder straps 46, the intermediate straps 48 and the harness bar 52 all attach to a bracket 54 which in turn attaches to a horizontal bar 16. A cable 56 is attached to each end of the horizontal bar 16. Each cable 56 extends around a pulley 58 attached to the top of the frame 12 and down around a second pulley 60 located on the end of a depending extension 59 which projects backward from the user proximate the upper horizontal member 18. The base of the cables 56 are attached to a biasing means 62, such as a spring, which provides the tension to support the upper body. Alternately, an elastic member such as a bungee cord may be substituted for the cable 56. The biasing means 62 is in turn fixedly attached to the frame 12. The configuration shown for the harness 40 is only an example of a working embodiment. Other configurations with differing numbers and configurations of straps and chest supporting sections are also envisioned. The front sections 44 are formed of a durable, flexible material. Although not required, a breathable material is preferred so that a user's perspiration will not be trapped by the material.

Two waist clips 34, are attached to the frame 12 proximate the lower horizontal member 22, and are used to attach the back support device 10 to the user's belt or pant waistband and holds the device in place while the user is donning the harness 40 and leg straps 30. The waist clips 34 are formed of any durable, flexible material, such as nylon, canvas, cotton, etc.

A buttocks support 36 extends between the two vertical members 14 and also between the lower intermediate horizontal member 20 and the lower horizontal member 22. The support 36 is preferably formed from canvas or other breathable material, but any desirable material may be used. The support 36 rests against the buttocks of the user.

At the bottom of the lower vertical member 24 are extension straps 31 which attach to leg straps 30. The leg straps 30 are formed of a durable, flexible material that is comfortable for the user to wear, preferably a breathable material so that a user's perspiration will not be trapped by the material. The straps 30 are attached around the user's legs, either above or below the knee, depending on the adjustment of the device and the height and preference of the user. The attachment means 32 is preferably formed from hook and loop fastener, but any other suitable attachment means may be used, including ties, buckles, snaps, etc. The extension straps 31 are a few inches long and allow some free leg movement while the user is upright, thereby allowing the user to walk.

The upper vertical members 25 are attached to the lower vertical sections 24 at a pivot point 26 by a rigid sleeve 28 that encloses the pivot point 26, the lowermost section of the upper vertical member 25 and the uppermost section of the lower vertical member 24, thereby making an essentially rigid connection. FIG. 3 shows a particular configuration for the pivot point 26 being formed from two hooks 70 which are free to pivot when the sleeve 28 is not in place. When the sleeve is moved away from the pivot point 26 the upper vertical member 25 and the lower vertical member 24 can pivot relative to one another. These may be a friction fit over the vertical members 24,25 or the sleeve 28 may be configured such that gravity holds the sleeve 28 over the pivot point 26 and against a projection 72 on the lower vertical member 24. When the user wishes to move freely, he or she moves the sleeve 28 up to engage a clip 74 or widened section of the upper vertical member 25. The sleeve 28 is then held out of the way until the user moves the sleeve 26 away from the clip 74.

FIG. 4 shows an optional manually adjustable tensioner 80 which allows the user to adjust the amount of tension to apply to the cable 56. If used, there are two tensioners, one located the lower ends of the cable 56. This adjustment may be used to adjust for different body types and different amounts of upper body weight A user may also choose to over or under compensate for their particular body. The tensioner 80 is a plate 82 having two holes 84, 86. The cable 56 runs through the first hole 84, which in this embodiment is round, and then through the second hole 86. In the embodiment shown, the second hole 86 is elongated. One end of the hole 86 is larger than necessary for the cable 56. When the user wishes to adjust the tension, the user pulls the cable 56 out of the narrow portion of the elongated hole 86 and into the widened section. This allows the cable 56 to slide freely. The user then selects the amount of tension desired by releasing more cable 56 or pulling in more cable 56 and pulls the cable 56 back into the narrow portion of the elongated hole 86, thereby locking the cable 56 into position and fixing a particular tension for the back support device 10. In this configuration the tensioner 80 is rigidly attached to the frame 12 and the springs 62 are not attached to the frame but are in the cable above the tensioner 80.

Figure 5:
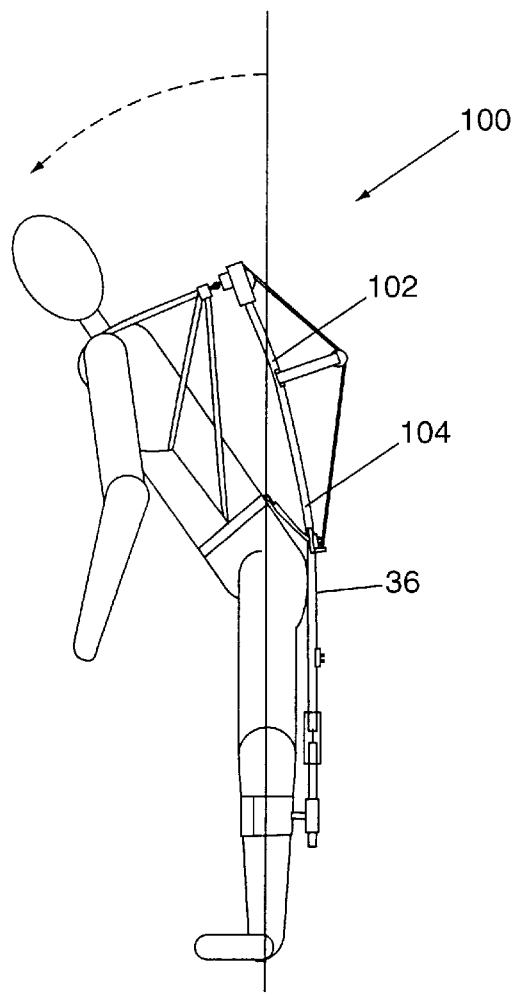
FIG. 5 is the side view of a person wearing the present invention using a flexible frame and cable system while bending forward.
Figure 6:
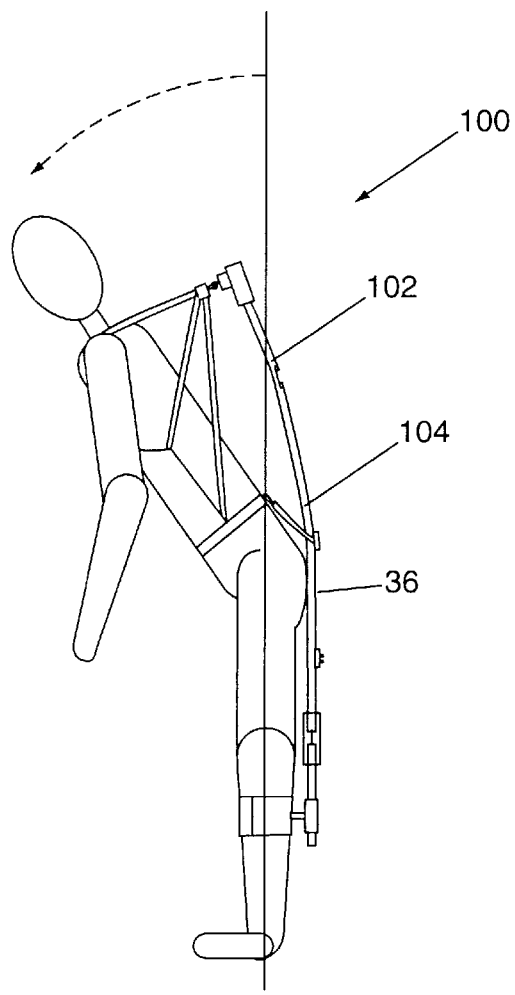
FIG. 6 is a side view of a person wearing the present invention using a flexible frame while bending forward.

FIG. 5 shows a resilient embodiment of the present invention. In this embodiment, part or all of the frame 104 is made of a resilient flexible material, such as fiberglass. The vertical members 102, at rest, are in a straight, vertical orientation. When a user bends over, his weight bends the members 102. The resilience of the material biases the members 102 towards their straight vertical position, thereby supporting the weight of the user's upper body and allowing the user to easily return to an upright position without significant effort. The resilient frame 104 allows the frame 104 itself to provide some or all of the back support. The resilient frame 104 may be used by itself as shown in FIG. 6, in which case the bracket would be attached directly to the frame 104, or it may be combined with a cable support system as is shown in FIG. 5.

Prior to beginning a task which requires a user to stoop, bend or be bent over, the user would don the back support device 10,100. It is currently believed that this is most easily accomplished by holding the back support device 10,100 at approximately the correct height and attaching the waist clips 34 to the user's belt or waistband. The leg straps 30 are then secured to the user's legs using the attachment means 32. Next, the arms are placed between the shoulder strap 46 and the intermediate strap 48 at which point the attachment means 42 is used to secure the front sections 44 of the harness 40 into place. At this point, the user would check the amount of tension to determine if it was appropriate for the intended use. If not, the user would adjust the tension. The user is now ready to work.

If the user wishes to walk around freely, without being encumbered by the back support device 10,100, the sleeves 28 are moved such that they no longer surround the pivot points 26. The lower vertical members 25 are now free to move in relation to the upper vertical members 25, thereby allowing the user free movement of the legs without movement of the entire back support device 10. This state may also be helpful during the donning process when the user bend to fastens on the leg straps 30.

In operation, when the user is stooped, the harness 40 supports the user's upper body weight. The harness 40 is in turn supported by the bracket 54 which may be fixedly attached to the resilient frame 104 or attached to the cable system shown in FIGS. 1 and 2. In either case, the weight of the upper body is transferred to the frame. The frame engages the lower body at the waist, the buttocks, and the legs, thereby transferring the weight of the upper body to the legs and buttocks.

Although the examples given include many specificities, they are intended as illustrative of only one possible embodiment of the invention. Other embodiments and modifications will, no doubt, occur to those skilled in the art. For example, the frame may be constructed with more or less vertical and horizontal members, a single cable could be used which is centered on the users back, etc. Thus, the examples given should only be interpreted as illustrations of some of the preferred embodiments of the invention, and the full scope of the invention should be determined by the appended claims and their legal equivalents.

I claim:

1. A back support device for supporting at least a portion of a user's upper body weight, said back support device comprising:
   a frame sized and configured to be located on a posterior portion of the user's body, said frame including first and second vertical members being configured to be located to the user's left and right sides, first and second horizontal members, each of said horizontal members extending from said first vertical member to said second vertical member,
   a buttock support attached to said frame,
   a harness sized and configured to engage the user's upper body, said harness being attached to said frame,
   a first leg attachment means depending from said frame,
   and a second leg attachment means depending from said frame.

2. The back support device of claim 1 wherein said frame is generally rigid.

3. The back support device of claim 1 wherein said frame is resilient.

4. The back support device of claim 1 wherein said buttock support extends between said first and second vertical members.

5. The back support device of claim 1 wherein said harness has at least one front panel forming at least a portion of a chest support surface, said chest support surface covering a majority of the user's chest.

6. The back support device of claim 1 wherein said buttock support is sized and configured to engage a majority of the user's buttocks.

7. The back support device of claim 1 wherein said harness is made of a breathable material.

8. The back support device of claim 1 wherein said frame is sized and configured to be worn offset from the user's body.

9. The back support device of claim 1 wherein said frame is made of fiberglass.

10. The back support device of claim 1 wherein said harness is attached to said frame by a cable.

11. The back support device of claim 1 wherein said frame is sized and configured to extend at least the full length of the back and buttocks.

12. The back support device of claim 1 wherein said first and second horizontal members hold said first and second vertical members in generally parallel orientation.

13. The back support device of claim 1 further comprising:
   an elastic cord having a first end and a second end, said first end connected to said harness and said second end connected to said frame,
   and a tension adjustment connecting one of said first end of said elastic cord to said harness and said second end of said elastic cord to said frame.

14. The back support device of claim 13 wherein said first end of said elastic cord is attached to said harness via a bracket and wherein said second end of said elastic cord is attached to said frame via an attachment means.

15. The back support device of claim 13 wherein said frame is made of fiberglass.

16. The back support device of claim 1 further comprising a biasing member which urges said harness toward said frame.

17. A back support device for supporting at least a portion of a user's upper body weight, said back support device comprising:
   a frame sized and configured to be located on a posterior portion of the user's body said frame comprising:
      first and second vertical members being configured to be located to the user's left and right sides, each of said vertical members having an upper portion and a lower portion,
      at least two horizontal members extending between said first and second vertical members,
      a first pivot point located intermediate said first and second portions of said first vertical member,
      a second pivot point located intermediate said first and second portions of said second vertical member,
      a first sleeve configured to surround said first pivot point, said first sleeve having a first position and a second position, wherein in said first position said first sleeve surrounds said first pivot point, thereby preventing said first pivot point from pivoting, and wherein in said second position, said first sleeve allows said pivot point to pivot, and a second sleeve configured to surround said second pivot point, said second sleeve having a first position and a second position, wherein in said first position said second sleeve surrounds said second pivot point, thereby preventing said second pivot point from pivoting, and wherein in said second position, said second sleeve allows said pivot point to pivot, a buttock support attached to said frame, a harness sized and configured to engage the user's upper body, said harness being attached to said frame, a first leg attachment means depending from said frame, and a second leg attachment means depending from said frame.

18. A back support device for supporting at least a portion of a user's upper body weight, said back support device comprising:

a frame sized and configured to be located on a posterior portion of the user's a buttock support attached to said frame, a harness sized and configured to engage the user's upper body, said harness being attached to said frame, a first leg attachment means depending from said frame.

a second leg attachment means depending from said frame, a bracket, wherein said harness is attached to said bracket, a cable having a first end and a second end, said first end of said cable being attached to said bracket, said second end being connected with said frame, and a pulley, an intermediate portion of said cable engaging said pulley, wherein said harness is attached to said frame by said bracket, said cable and said pulley.

19. The back support device of claim 18 wherein said frame comprises:

a first vertical member and a second vertical member being configured to be located to the user's left and right sides, each of said vertical members having an upper portion and a lower portion, at least two horizontal members extending between said first and second vertical members, said buttock support extends between said first and second vertical members, a biasing means, attached to said second end of said cable, said first leg attachment means depending from said first vertical member, said second leg attachment means depending from said second vertical member, a first pivot point located intermediate said first and second portions of said first vertical member, a second pivot point located intermediate said first and second portions of said second vertical member, a first sleeve configured to surround said first pivot point, said first sleeve having a first position and a second position, wherein in said first position said first sleeve surrounds said first pivot point, thereby preventing said first pivot point from pivoting, and wherein in said second position, said first sleeve allows said pivot point to pivot, a second sleeve configured to surround said second pivot point, said second sleeve having a first position and a second position, wherein in said first position said second sleeve surrounds said second pivot point, thereby preventing said second pivot point from pivoting, and wherein in said second position, said second sleeve allows said pivot point to pivot.

* * * * *